United States Patent [19]

Paul

[11] Patent Number: 4,817,789

[45] Date of Patent: Apr. 4, 1989

[54] LENS CONTAINER ASSEMBLY

[75] Inventor: Lyle E. Paul, El Toro, Calif.

[73] Assignee: Allergan, Inc., Irvine, Calif.

[21] Appl. No.: 100,297

[22] Filed: Sep. 23, 1987

[51] Int. Cl.$^4$ ............................................. B65D 85/38
[52] U.S. Cl. ...................................... 206/5.1; 206/438
[58] Field of Search ................... 206/5, 5.1, 210, 438; 623/6

[56] References Cited

U.S. PATENT DOCUMENTS

| | | |
|---|---|---|
| 3,298,502 | 1/1967 | Schwartzman ........................ 206/5 |
| 3,977,517 | 8/1976 | Kadlecik et al. ..................... 206/5.1 |
| 4,091,917 | 5/1978 | Clawson ............................... 206/5.1 |
| 4,113,088 | 9/1978 | Binkhorst . |
| 4,173,281 | 11/1979 | Trought . |
| 4,205,747 | 6/1980 | Gilliam et al. . |
| 4,257,521 | 3/1981 | Poler . |
| 4,269,307 | 5/1981 | LaHaye . |
| 4,402,396 | 9/1983 | Graham . |
| 4,423,809 | 1/1984 | Mazzocco . |
| 4,508,216 | 4/1985 | Kelman . |
| 4,615,703 | 10/1986 | Callahan ............................. 206/5.1 |
| 4,684,014 | 8/1987 | Davenport ........................... 206/5.1 |
| 4,697,697 | 10/1987 | Graham et al. ..................... 206/438 |
| 4,736,836 | 4/1988 | Alongi et al. . |

*Primary Examiner*—Jimmy G. Foster
*Attorney, Agent, or Firm*—Frank J. Uxa, Jr.; Gordon L. Peterson

[57] ABSTRACT

A lens container assembly comprising:

a lens container acting to hold a lens, and including a base and a lens cover movable relative to the base and acting together with the base to form a compartment of sufficient size to contain the lens;

a carrier acting to carry the lens container and being movable so that by moving the carrier, the lens container is placed in a closed position with the lens cover in relative proximity to the base or in an opened position with the lens cover relatively separated from the base; and a housing acting to hold the carrier and being adapted so that the carrier is movable relative thereto, the housing including a cam acting to at least assist in moving the lens container to the opened position.

43 Claims, 4 Drawing Sheets

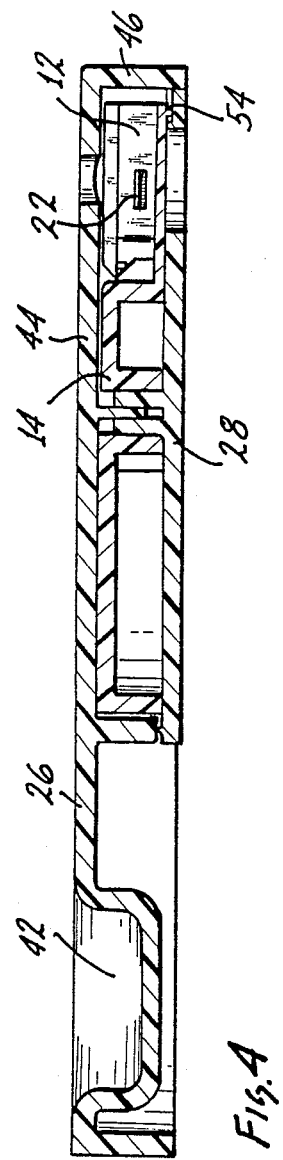
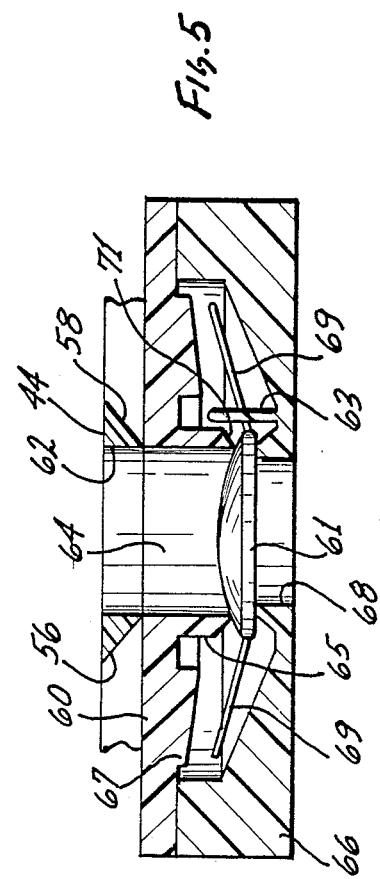
Fig. 4
Fig. 5

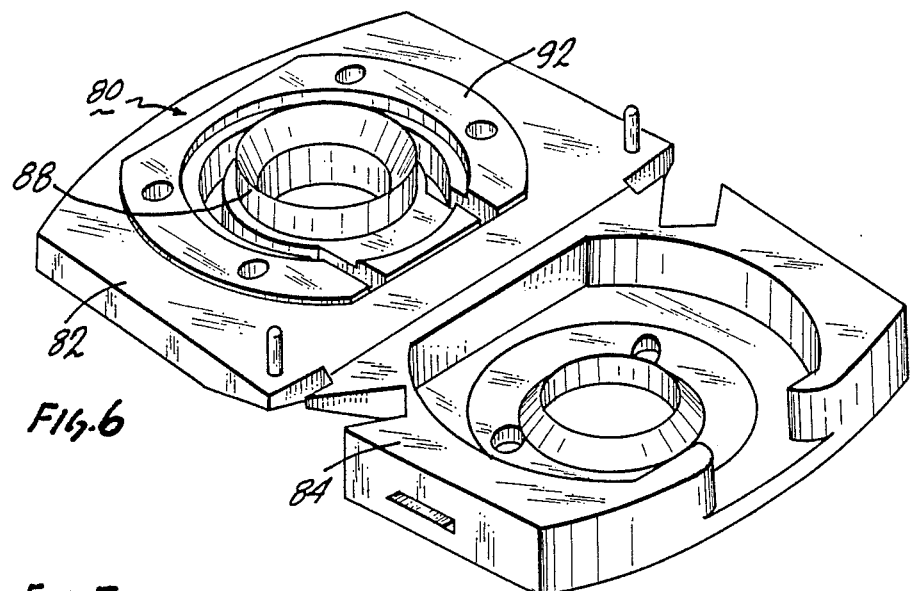
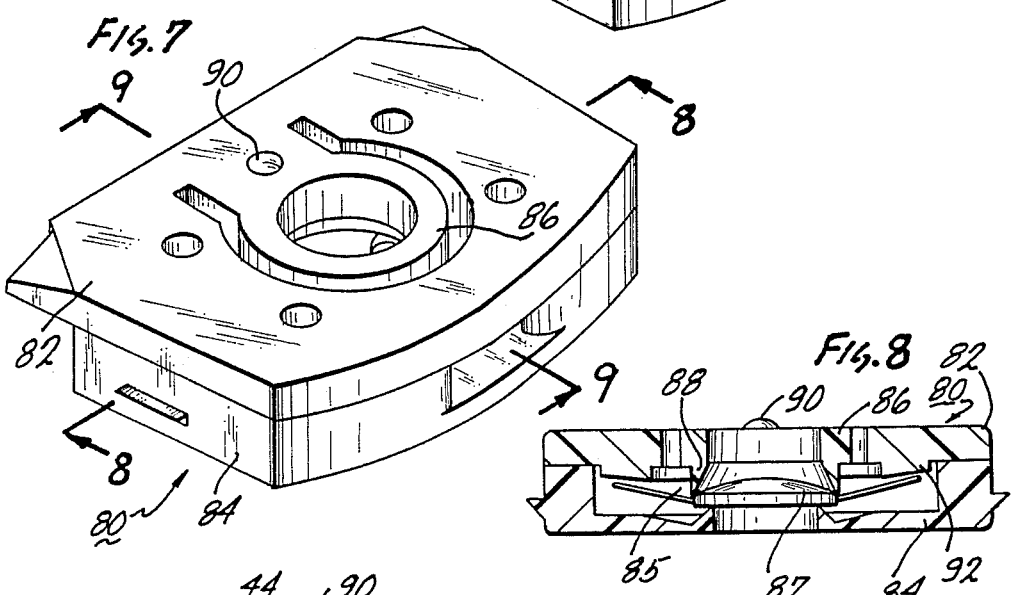
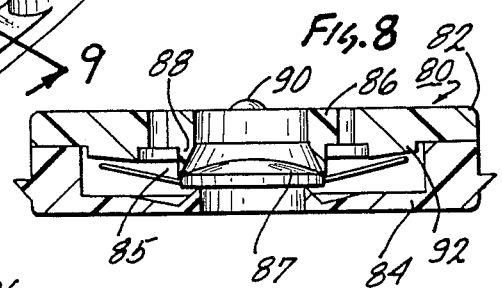
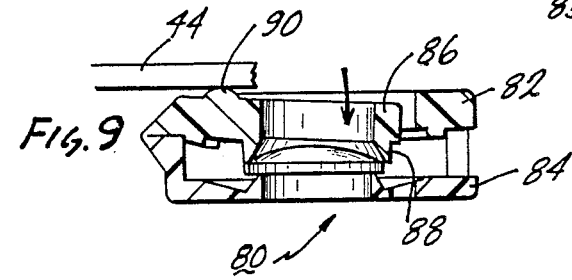

LENS CONTAINER ASSEMBLY

BACKGROUND OF THE INVENTION

This invention relates to a lens container assembly. More particularly, the invention relates to such an assembly, especially suited for intraocular lens, which effectively protects the lens during storage while providing rapid and easy access to the lens when it is needed.

Artificial lenses, such as contact lenses, intraocular lenses and the like, are becoming more and more useful in correcting vision problems. For example, intraocular lenses can be surgically implanted in the eyes of alhakic patients, i.e., patients who do not have natural lenses.

An intraocular lens is often packaged in a sterile container, e.g., plastic pouch and the like, to insure that the lens itself is sterile prior to surgery. However, once this outer container is ruptured, e.g., inside the surgical suite, there is still the need to provide the lens in a container which makes it easy and convenient for the surgical team to obtain access to the lens for implantation. The container should effectively protect the lens prior to withdrawing the lens from the container. The container also should facilitate any processing, e.g., irrigation, sterilization and the like, of the lens which is necessary or desirable to be done in the surgical suite prior to implantation.

A number of lens packages and containers have been disclosed previously. See, for example, U.S. Pat. Nos. 4,113,088; 4,173,281; 4,205,747; 4,257,521; 4,269,307; 4,402,396; 4,423,809; and 4,508,216. A number of these patents, e.g., U.S. Pat. Nos. 4,113,088; 4,257,521; 4,173,281 and 4,423,809 are directed primarily to the outer, sterile package referred to above and/or to a combination outer sterile package/lens container. The other above-noted patents disclose lens containers. A number of the prior lens containers involve "snap" or "twist" type caps which may create sudden and uneven motion resulting in an increased likelihood that the lens will fall out of the container or be otherwise damaged. Many of these previous devices are relatively bulky and/or mechanically complex and, thus, require both hands of a surgical nurse/assistant in order to gain access to the lens for implantation. Thus, using these devices, the surgical nurse/assistant is substantially fully occupied in handling the lens container.

It would clearly be advantageous to provide a lens container assembly capable of being operated effectively and efficiently by surgical personnel.

SUMMARY OF THE INVENTION

A new lens container assembly has been discovered. In one broad aspect, the present assembly includes three subsystems: a lens container; a carrier; and a housing.

The lens container sub-system or means acts to hold the lens, and includes a base and a lens cover which is moveable relative to the base and together with the base acts to form a compartment of sufficient size to contain the lens. The lens cover is used to protect the lens while the lens container is in a closed position. In one particularly useful embodiment, the lens container includes a clamp means movable relative to the base means and adapted to be activated with the lens container in a closed position to hold the lens in place in the compartment. The carrier sub-system acts to carry the lens container and is moveable relative to the housing so that by moving the carrier means the lens container can be placed into a closed position with the lens cover in relative proximity to the base or in an opened position with the lens cover is relatively separated from the base. The housing sub-system acts to hold the carrier. The housing includes a cam mechanism which at least assists in moving the lens container to its opened position or positions.

The present lens container assembly provides substantial advantages. For example, the lens cover very effectively protects the lens from damage while the lens container sub-system is in a closed position and as it is moved to an opened position. The movement of the carrier vis-a-vis the housing is relatively smooth, thus reducing still further the possibility that the lens will be damaged in or drop out of the lens container. No "snap" type or threaded "twist" type caps, such as employed in certain of the above-noted previous lens container devices, are required here. The present assembly is preferably structured to be held, and more preferably operated, by one hand of an adult human. Also, the system can preferably be operated by either the right hand or the left hand of an individual. The lens container, e.g., including the movable clamp means, is preferably structured to be useful with different sized lenses. This is important since lenses come in a large number of sizes. Having a lens container usable with different sized lenses avoids the manufacturing problems and costs involved in producing a separately configured lens container for each differently sized lens. These features allow for the present lens container assembly to be used with great effectiveness, efficiency and flexibility in the surgical suite.

In short, the lens container assembly of the present invention protects the lens prior to use, allows easy and rapid access to the lens when needed, and facilitates efficiency during the lens implantation surgery.

It is preferred that the lens container be moveable to a first opened position and a second opened position, as desired. This feature provides additional flexibility. For example, a right handed person may choose to employ the first opened position to gain access to the lens, while a left handed person may choose to employ the second opened position, or vice versa. Preferably, the assembly is structured so that lens container is moved to the closed position after being in either the first or second opened positions prior to being placed in the other opened position. This feature provides for increased protection of the lens in the lens container and reduces the risk of the lens falling out of the container.

The lens container may be an integral part of the carrier, or it may be structured to be removable from the carrier. In this latter embodiment, the carrier is preferably structured to receive and hold lens containers having different configurations. This adds to the flexibility of the present system since there are a substantial number of differently configured intraocular lenses, each of which may require, or at least benefit from a differently configured lens container.

The lens container itself is preferably a single integral item, e.g., made from a resilient material such as molded polymeric material, in particular polyolefin, especially polypropylene.

Where the lens container includes a movable clamp means, it is preferred that the clamp means, upon being activated, physically contacts the lens in the compartment. In this manner, the clamp means physically holds or secures the lens in the compartment. The movable clamp means may be attached to the base and/or the lens cover. The base and the lens cover are preferably secured together at at least one point. The clamp means may be activated by the action of a cam. For example, the lens cover, or the housing of the present lens container assembly, may include at least one projection adapted to be contacted with the lens container in a closed position to facilitate the activation of the clamp means. The projection is contacted by the housing or the lens cover as the lens cover moves to a closed position. This cam action, in turn, activates the clamp means to hold the lens in place in the compartment of the lens container. The projection is preferably located between the point or points of securement of the base and the lens cover, and the vertical, central axis of the compartment. In this embodiment the force on the projection is applied indirectly to the lens in the compartment. This allows a degree of "cushioning" of this force on the lens, in particular when, as is preferred the lens cover is constructed of resilient material, and protects the lens from being damaged.

As noted above, the carrier sub-system carries the lens container and is movable relative to the housing so that the lens container can be moved between opened and closed positions. The carrier may be slidable relative to the housing. However, it is preferred that the carrier be rotatable relative to the housing. Such rotatability allows the carrier to be easily manipulated, e.g., by the same hand holding the entire assembly, so that the lens container can be moved between closed and opened positions, as desired.

The housing of the present assembly includes a cam element or means which acts to at least assist in moving the lens container to an opened position. Such cam element is preferably stationary and comes into contact with the lens container as the carrier moves relative to the housing. Preferably, the number of cam elements included is equal to the number of opened positions of the lens container. The housing preferably further includes a closing element or means which acts to at least assist in moving the lens container to a closed position. More preferably, the closing element further acts to at least partially maintain, e.g., by mechanical force, the lens container in a closed position. The lens container, and in particular the cover of the lens container, includes at least one projection acting to contact the cam as the carrier is moved to place the lens container means in an opened position. The number of projections of bumps on the lens container is preferably equal to the number of opened positions of the lens container and/or the number of cams.

The housing, carrier and the lens container each preferably includes at least one aperture to allow the lens being held by or in the lens container to be irrigated, e.g., for sterilization purposes and the like, with the lens container in a closed position. Thus, the lens can be sterilized or otherwise treated, as needed or desired, while the lens remains securely located in the lens container of the present assembly.

The housing preferably further includes a soaking tray sized and adapted to allow a lens, more preferably an intraocular lens, to be immersed in liquid. Thus, in this embodiment, the assembly provides a very convenient place for the lens to be washed, or otherwise treated outside the lens container. This soaking tray is preferably included without adversely affecting the size and/or shape or configuration of the assembly, which preferably is sized to be held in one hand of an adult human.

Whereas the lens container is preferably made at least partially from a resilient material, the present carrier and housing are preferably made of substantially rigid materials, e.g., substantially rigid polymeric materials. The carrier and housing may be substantially transparent and/or may be colored for cosmetic reasons. One particularly useful class of materials of construction of the carrier and housing are the polycarbonates and mixtures thereof.

The present assembly preferably further comprises a lock sub-system or means acting to lock the lens container in a closed position, more preferably in an opened position or in a closed position, as desired. This lock allows the lens container to be maintained in an opened position, e.g., so that the lens contained therein can be easily accessed, or in a closed position, e.g., to provide effective protection for the lens during storage, shipment and the like. The lock is preferably such that the lens container can be moved out of the "locked" closed position or out of the "locked" opened position by the application of manual force, preferably by such manual force as can be generated by the same adult human hand holding the assembly. In a particularly useful embodiment, the carrier includes one portion, preferably a bump or projection, of the lock sub-system and the housing carries another portion, e.g., one or more, more preferably three, grooves or notches, of the lock sub-system. The two portions engage or mate together to activate the lock. When the two lock portions are not engaged, the lock sub-system is not activated. If three grooves or notches are employed, the lens container means preferably has two opened positions, e.g., a first opened position and a second opened position, and one closed position.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 4 is a cross-sectional view taken along line 4—4 in FIG. 1.

FIG. 5 is a cross-sectional view taken along line 5—5 in FIG. 1.

FIG. 6 is a top side view, in perspective, of an alternate embodiment of a lens container.

FIG. 7 is a top side view, in perspective, of the embodiment shown in FIG. 6 is a closed position.

FIG. 8 is a cross-sectional view taken along line 8—8 in FIG. 7.

FIG. 9 is a cross-sectional view taken along line 9—9 in FIG. 7.

DETAILED DESCRIPTION OF THE DRAWINGS

Figure 1:
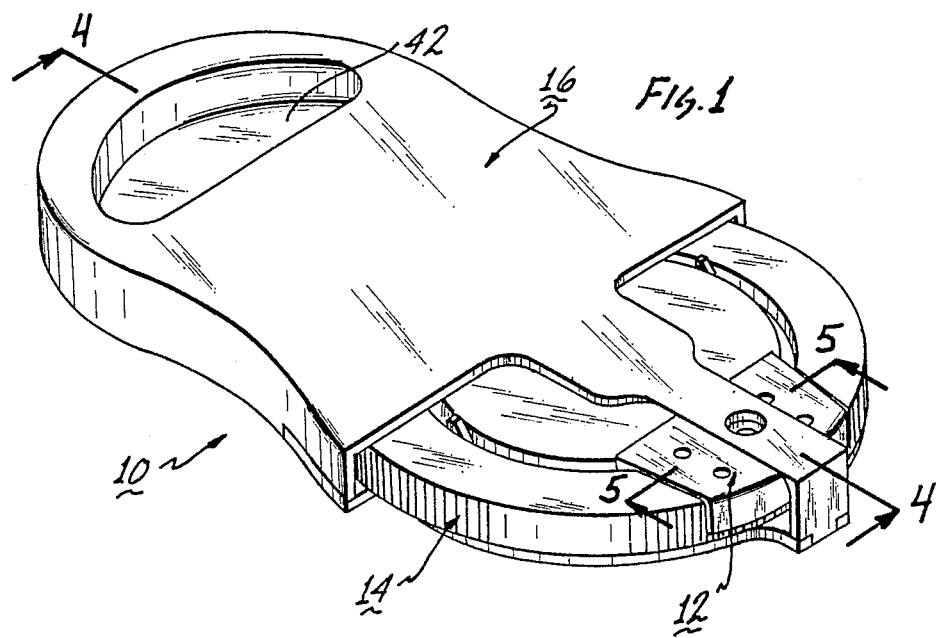
FIG. 1 is a top side view, in perspective, of one embodiment of the present lens container assembly showing the lens container in a closed position.

Referring now to the drawings, a lens container assembly, shown generally at 10, includes a lens container 12, a carrier 14 and a housing 16.

Figure 3:
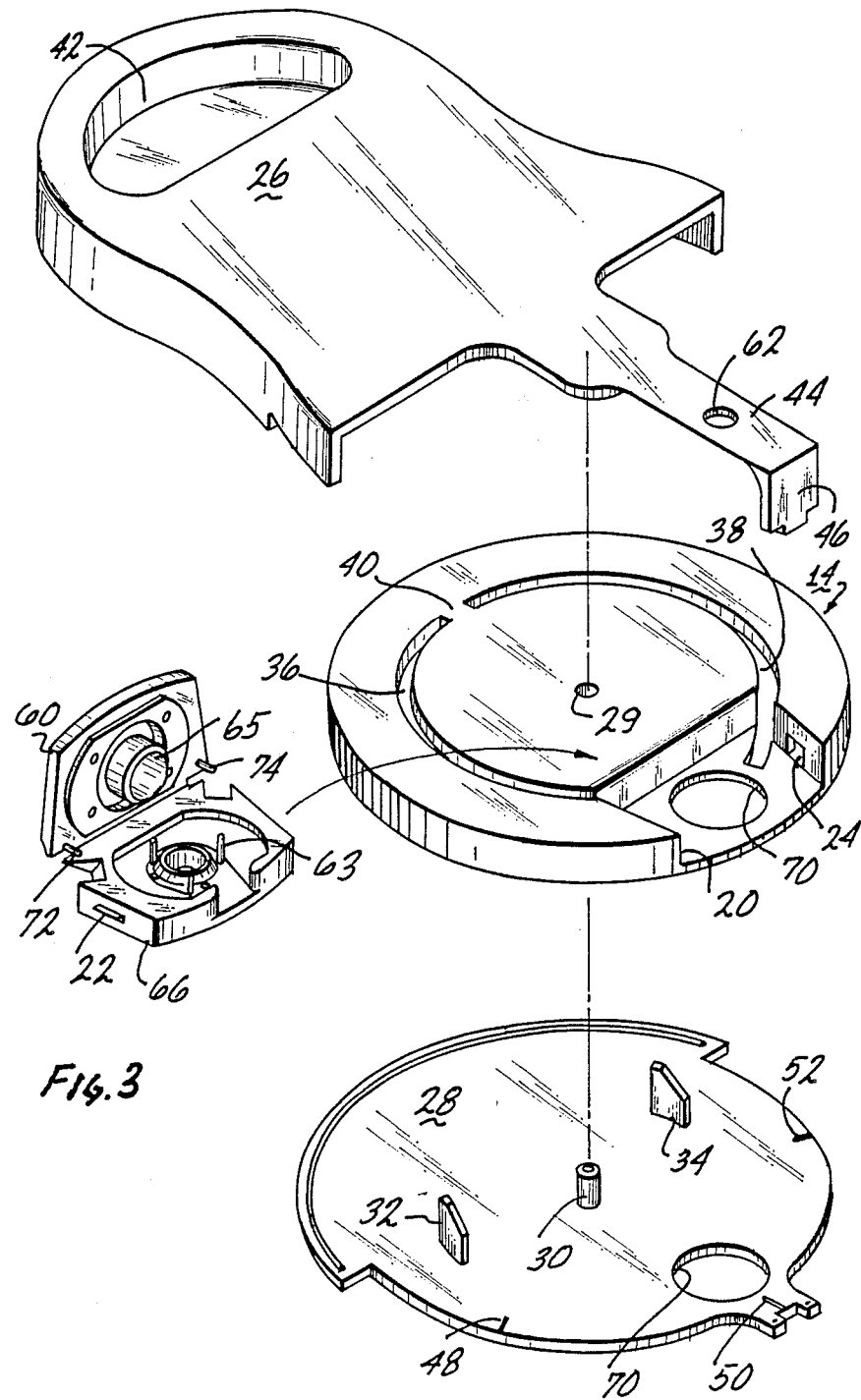
FIG. 3 is a blown apart view, in perspective, of the embodiment shown in FIG. 1.

As shown best in FIG. 3, lens carrier 12 is removable from carrier 14. This allows the use of differently configured lens containers 12 in combination with carrier 14 and housing 16. This is useful since intraocular lenses have various configurations each of which often require a specifically structured lens container 12. Thus, the only element of lens assembly 10 which may need to be changed to accommodate a wide variety of lenses is lens container 12. Lens container 12 is removably secured in place in space 20 of carrier 14 by snapping taps 22, located on both sides of lens container 20, into holes 24 located in both sides of space 20.

Housing 16 is made up of a top 26 and a base 28. A peg 30 extends from base 28 through hole 29 in carrier 14 and is secured, e.g., adhesively or otherwise secured, to top 26. In this manner carrier 14 is rotatable (but not fully rotatable) in either the clockwise or counter-clockwise direction relative to housing 16.

Base 28 further includes a first cam 32 and a second cam 34 which extend from base 28. With peg 30 secured to top 26, first cam 32 and second cam 34 extend into first channel 36 and second channel 38, respectively, of carrier 14. First channel 36 and second channel 38 terminate separately at one end in space 20 and, at the other end are separated by solid portion 40 of carrier 14. The limited lengths of first channel 36 and second channel 38 combined with the first cam 32 and second cam 34 which protrude into first channel 36 and second channel 38, respectively, act to limit the rotation of carrier 14 relative to housing 16.

Housing 16 is sized and contoured to be capable of being easily held in and by the palm and fingers of an adult human. Top 26 of housing 16 includes a soak basin 42 which is useful to fill with a suitable liquid so as to soak or otherwise treat the intraocular lens before implantation. Top 26 also includes a forwardly extending finger 44 which, in turn, includes a depending member 46 adapted to be fit into and secured to base 28.

Base 28 includes three spaced apart grooves or notches 48, 50 and 52. As best seen in FIG. 4, carrier 14 includes a downwardly depending projection or bump 54 which is sized to be received and held in any one of notches 48, 50 and 52. When bump 54 is received and held in one of notches 48, 50 and 52, carrier 14 is "locked" relative to housing 16. In other words, when bump 54 is in one of notches 48, 50 and 52, carrier 14 is locked in place relative to housing 16. Carrier 14 can be "unlocked" very simply, e.g., by manually applying sufficient rotational force to carrier 14 to extricate bump 54 from the notch which is holding it. During periods of storage, bump 54 is held by notch 50. When lens container is in the first opened position, bump 54 is in notch 48, and when lens container 12 is in the second opened position, bump 54 is in notch 52.

As best seen in FIG. 5, finger 44 includes sidewalls 56 and 58 each of which slant in. This slanting is useful to assist in closing the cover 60 of lens container 12 as lens container 12 is moved to the closed position.

Finger 44 includes a through hole 62; cover 60 includes a through hole 64; lens container base 66 includes through hole 68; and base 28 includes a through hole 70. When lens container 12 is in the closed position, all of the through holes noted in this paragraph are in mutual alignment. In this configuration, lens container assembly 10 is very suitable for sterilizing or otherwise treating the intraocular lens contained in lens container 12. These through holes allow fluid to pass in contact with the lens to provide the desired treatment.

As noted previously, lens container 12 is specially configured to hold an intraocular lens having a defined structure. A different lens container 12 may be required depending on the specific structure of the lens. As best seen in FIG. 5, the lens 61 is preferably placed on lens container base 66 between the posts 63 which extend upwardly from base 66 and aid in confining lens 61. Cover 60 includes a downwardly extending optic constraint ring 65. When cover 60 is placed so that lens container 12 is in the closed position, see FIG. 5, a compartment 71 is formed between cover 60 and lens container base 66 of suitable size to receive and hold lens 61. Optic constraint ring 65 terminates between posts 63, below the tops of posts 63 and above lens 61, and acts to aid in holding lens 61 is place. Optic constraint ring 65 extends downwardly low enough to effectively prevent any tilting of lens 61. Also, the center thickness of lens 61 is greater than the clearance between the termination of optic constraint ring 65 and lens 61. A separate loop constraint ring 67 extends downwardly from cover 60 and acts to maintain the attachment loops 69 of lens 61 in place when lens container 12 is in the closed positon. Lens container 12 is structured to hold lens 61 including attachment loops 69 which extend outwardly from the lens body at an angle of about 10°. Other lens containers, similiar in structure and functioning similarly to lens container 12, can be made to accommodate other lens configurations, such as flat lenses and vaulted lenses. These other lens containers may be used in lens container assembly 10.

Figure 2:
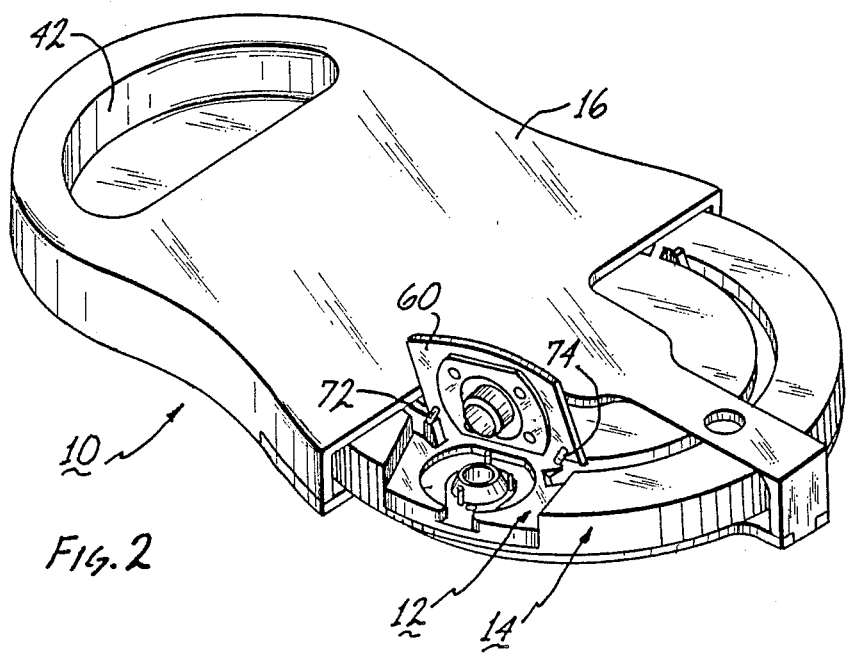
FIG. 2 is a top side view, in perspective, of the embodiment shown in FIG. 1 showing the lens container in an opened position.

As best seen in FIGS. 2 and 3, cover 60 includes a first projection 72 and a second projection 74 which co-act with first cam 32 and second cam 34, respectively to assist in moving lens container 12 into the first opened position and the second opened position, respectively. As carrier 14 is rotated in a clockwise direction from a point where lens container 12 is in the closed position, first projection 72 comes into contact with first cam 32. As carrier 14 continues to be rotated, first projection 72 is caused to ride up the top surface of first cam 32, thereby moving lens container 12 into the first opened position. Similarly, as carrier 14 is rotated in a counterclockwise direction from a point where lens container 12 is in the closed position, second projection 74 comes into contact with second cam 34. As carrier 14 continues to rotated, second projection 74 is caused to ride up the top surface of second cam 34, thereby moving lens container 12 into the second opened position The slanting sidewalls of finger 44 and the cam-projection combinations discussed directly above provide for smooth transitions for lens container 12 from opened to closed positions and vice versa. Lens container assembly 10 can be effectively operated to provide access to the intraocular lens contained in lens container 12 without undue risk that the lens will fall out because of any abrupt movement being required to open or close lens container 12.

Lens container 12 is preferably made as one piece of resilient material, more preferably polypropylene. The other components of lens container assembly 10 are preferably made of a rigid material, more preferably polycarbonate.

Lens container assembly 10 functions as follows. An appropriate lens container 12 is selected based on the structure of the intraocular lens to be packaged/implanted. This appropriate lens container 12 is secured to carrier 14, as described above, and lens container 12 is moved to an opened position.

The intraocular lens is put in place on lens container base 66 and lens container 12 is moved to the closed position. While lens container 12 is in the closed position, the intraocular lens is sterilized and/or otherwise treated so as to be ready for implantation.

In the surgical suite itself, the lens may again be sterilized and/or otherwise treated in preparation for the implantation procedure.

When the surgeon is ready for the lens, a surgical assistant takes lens container assembly 10 into his/her hard and with his/her thumb moves carrier 14 so that lens container 12 moves from the closed position to either first or second opened position. Lens container assembly 10 can be effectively operated by either a right or left handed person.

With lens container 12 in an opened position, the surgeon can remove the lens. If necessary, the lens can be soaked in soak basin 42. In any event, once the lens has been removed from lens container 12, it is ready to be implanted. Lens container assembly 10 has served its purpose.

As noted previously, lens container 12 is structured to be used with a specifically sized lens 61. FIGS. 6, 7, 8 and 9 illustrate a second lens container, shown generally at 80, which is structured to be useful with various sizes of lenses. Unless otherwise expressly set forth herein, second lens container 80 is structured and functions, e.g., in place of lens container 12 in lens container assembly 10, similiarly to lens container 12. In addition, second lens container 80 is preferably constructed of the same materials preferred for the construction of lens container 12.

Second lens container 80 includes a cover portion 82 and a base portion 84. When second lens container 80 is in the closed position, cover portion 82 and base portion 84 form a compartment 85 in which second lens 87 can be received and held ready for use. Top portion 82 includes a flexible arm 86 which, in turn, includes a downwardly depending lens contact ring 88 which acts to hold or clamp second lens 87 in place in compartment 85. Top portion 82 includes a loop restraining ring 92 which functions in much the same way as does loop constraint ring 67, discussed previously. The top surface of top portion 82 includes an outwardly extending bump 90.

Second lens container 80 function's as follows. With second lens container 80 in an opened position, second lens 87 is placed in the center of compartment 85. As second lens container 80 is moved to the closed position, finger 44 comes into contact with bump 90. This cam action, in turn, causes lens contact ring 88 to move into contact with second lens 87, thereby holding second lens 87 in place. Bump 90 is positioned away from second lens 87 so that the resiliency or flexibility of flexible arm 86 acts to cushion the force exerted on second lens 87 as bump 90 contacts or rides on finger 44. Note that base portion 84 does not include any posts. A wide variety of different sized lenses can be used with a single second lens container 87. It may be advantageous to provide different lens containers, structured analogously to second lens container 80, for flat lenses and vaulted lenses.

The present lens container assembly is very effective in protecting lenses, in particulary intraocular lenses. The system is reliably and smoothly moved from the closed position where the lens is very well protected to an opened position where the lens is readily accessible to the surgeon. The assembly can be held and operated by one hand and, preferably can be just as easily operated by either right or left handed people. In short, the present assembly is relatively simple in structure, effective for its intended purpose, and easy and flexible in its operation.

While this invention has been described with respect to various specific examples and embodiments, it is to be understood that the invention is not limited thereto and it can be variously practiced within the scope of the following claims.

What is claimed is:

1. A lens container assembly comprising:

lens container means acting to hold a lens, and including a base means, and a lens cover means moveable relative to said base means and acting together with said base means to form a compartment of sufficient size to contain said lens;

carrier means acting to carry said lens container means and being movable so that by moving said carrier means said lens container means is placed in a closed position with said lens cover means in relative proximity to said base means or in an opened position with said lens cover means relatively separated from said base means; and housing means acting to hold said carrier means and being adapted so that said carrier means is movable relative thereto, said housing means including cam means acting to at least assist in moving said lens container means to said opened position.

2. The assembly of claim 1 wherein said housing means further includes closing means acting to at least assist in moving said lens container means to said closed position.

3. The assembly of claim 1 wherein each of said lens container means, said carrier means and said housing means includes at least one aperture to allow said lens held by said lens container means to be irrigated with said lens container means in said closed position.

4. The assembly of claim 1 wherein said lens container means is at least partially made of resilient material.

5. The assembly of claim 4 wherein said carrier means and said housing means are made of substantially rigid material.

6. The assembly of claim 5 wherein said lens container means is made of polyolefin, and said carrier means and said housing means is made of polycarbonate.

7. The assembly of claim 1 wherein said lens container means is capable of being moved to a first opened position and a second opened position.

8. The assembly of claim 7 wherein said carrier means is rotatable relative to said housing means.

9. The assembly of claim 8 which is sized and adapted to be held in one hand of an adult human.

10. The assembly of claim 7 which is structured so that said lens container means is moved to said closed position after being in either said first or second opened positions prior to being placed in the other of said first or second opened positions.

11. The assembly of claim 1 wherein said lens container means includes at least one first projection acting to contact said cam as said carrier means is moved to place said lens container means in said opened position.

12. The assembly of claim 1 wherein said carrier means is rotatable relative to said housing means.

13. The assembly of claim 12 which is sized and adapted to be held in one hand of an adult human.

14. The assembly of claim 1 wherein said housing means includes a soaking tray sized and adapted to allow an intraocular lens to be immersed in liquid.

15. The assembly of claim which further comprises lock means acting to lock said lens container means in at least one of said opened position and said closed position, as desired.

16. The assembly of claim 15 wherein said lock means is capable of acting to lock said base container means in both said opened position and said closed position, as desired, and includes a bump located on either of said housing means or said carrier means and at least two grooves located on the other of said housing means or said carrier means, said bump capable of being received by and held in any of said grooves to render said carrier means substantially immovable relative to said housing means.

17. The assembly of claim 1 which is sized and adapted to be held in one hand of an adult human.

18. The assembly of claim 17 wherein said carrier means is of being moved relative to said housing means by the same one hand of an adult human being used to hold said assembly.

19. The assembly of claim 1 wherein said lens container means is structured to be removable from said carrier means.

20. The assembly of claim 19 wherein said carrier means is structured to receive and hold different lens carrier means having different configurations.

21. The assembly of claim 1 which is structured to contain one intraocular lens.

22. The assembly of claim 1 wherein said lens container means is a single integral item.

23. The assembly of claim 1 wherein said lens container means further comprises clamp means movable relative to said base means and adapted to be activated with said lens container means in said closed position to hold said lens in place in said compartment.

24. The assembly of claim 23 wherein said lens container means is useful with different sized lenses.

25. The assembly of claim 24 wherein said base means is adapted to accommodate different sized lenses and said movable clamp means upon being activated physically contacts said lens in said compartment, said movable clamp means being associated with a flexible activation arm to cushion said physical contact of said movable clamp means with said lens.

26. The assembly of claim 25 wherein said base means defines a substantially unobstructed space.

27. The assembly of claim 23 wherein said movable clamp means upon being activated physically contacts said lens in said compartment.

28. The assembly of claim 23 wherein said clamp means is attached to said lens cover means.

29. The assembly of claim 28 wherein said lens cover means is constructed of resilient material.

30. The assembly of claim 29 wherein said lens cover means and said base means are secured together at at least one point.

31. The assembly of claim 20 wherein said lens cover means or said housing means further includes at least one second projection adapted to be contacted with said lens container means in said closed position to facilitate the activation of said clamp means.

32. The assembly of claim 31 wherein said second projection is located between the point or points of securement between said base means and said lens cover means, and the vertical, central axis of said compartment.

33. The assembly of claim 23 wherein said clamp means is activated by the action of a cam.

34. A lens container for holding a lens comprising:
base means;
lens cover means constructed of resilient material, secured to said base means at at least one point and together with said base means acting to form a compartment of sufficient size to contain a lens;
clamp means attached to said lens cover means, being movable relative to said base means and said lens cover means and adapted to be activated to hold said lens in place in said compartment and;
projection means secured to said lens cover means and adapted to be contacted to activate said clamp means.

35. The lens container of claim 34 which is useful with different sized lenses.

36. The lens container of claim 34 wherein said clamp means upon being activated physically contacts said lens in said compartment.

37. The lens container of claim 34 wherein said projection means is located on said cover means between the point or points of securement between said cover means and said base means and the vertical, central axis of said compartment.

38. The lens container of claim 34 which is structured so that both said base means and said clamp means contact said lens to hold said lens in place in said compartment and substantially prevent movement of said lens.

39. A lens container for holding a lens comprising:
base means;
lens cover means associated with said base means and together with said base means acting to form a compartment of sufficient size to contain a lens; and
clamp means being movable relative to said base means and said lens cover means and adapted to be activated by the action of a cam to hold said lens in place in said compartment.

40. The lens container of claim 39 wherein said clamp means is attached to said lens cover means.

41. The lens container of claim 40 wherein said lens cover means is constructed of resilient material.

42. The lens container of claim 39 wherein said lens cover means and said base means are secured together at at least one point.

43. The lens container of claim 39 which is structured so that both said base means and said clamp means contact said lens to hold said lens in place in said compartment and substantially prevent movement of said lens.

* * * * *

UNITED STATES PATENT AND TRADEMARK OFFICE
CERTIFICATE OF CORRECTION

PATENT NO. : 4,817,789

DATED : Apr. 4, 1989

INVENTOR(S) : Lyle E. Paul

It is certified that error appears in the above-identified patent and that said Letters Patent is hereby corrected as shown below:

Column 9, line 10 change "claim which" to -- claim 1 which --.

Signed and Sealed this

Seventeenth Day of October, 1989

Attest:

DONALD J. QUIGG

Attesting Officer

Commissioner of Patents and Trademarks